(12) United States Patent
McCrea

(10) Patent No.: US 7,146,850 B2
(45) Date of Patent: Dec. 12, 2006

(54) ROLL CONTOUR MEASURING APPARATUS AND METHOD

(75) Inventor: Keith A. McCrea, Yorkville, OH (US)

(73) Assignee: Chrome Deposit Corporation, Monroe, OH (US)

( * ) Notice: Subject to any disclaimer, the term of this patent is extended or adjusted under 35 U.S.C. 154(b) by 112 days.

(21) Appl. No.: 10/616,472

(22) Filed: Jul. 8, 2003

(65) Prior Publication Data

US 2005/0005687 A1    Jan. 13, 2005

(51) Int. Cl.
*G01B 5/28* (2006.01)
(52) U.S. Cl. .......................................... 73/105
(58) Field of Classification Search .................. 73/105, 73/149, 865.8, 866.5, 620, 596, 597, 598, 73/621, 622, 618, 633, 634; 324/207.24, 324/207.22, 228, 229, 230–243, 207.11, 662; 356/2, 600, 601, 614, 635, 636
See application file for complete search history.

(56) References Cited

U.S. PATENT DOCUMENTS

| | | | | |
|---|---|---|---|---|
| 3,939,404 A * | 2/1976 | Tait | ................ | 324/224 |
| 4,053,237 A | 10/1977 | Casey | ................ | 356/209 |
| 4,423,636 A | 1/1984 | Plante | ................ | 73/622 |
| 4,495,587 A | 1/1985 | Plante et al. | ................ | 364/507 |
| 4,959,553 A * | 9/1990 | Yamada et al. | ........ | 250/559.24 |
| 5,117,081 A | 5/1992 | Bagdal | ................ | 219/69.1 |
| 5,212,452 A * | 5/1993 | Mayer et al. | ................ | 324/662 |
| 5,505,682 A | 4/1996 | Shimizu | | |
| 5,533,401 A * | 7/1996 | Gilmore | ................ | 73/622 |
| 5,563,808 A * | 10/1996 | Tuck et al. | ................ | 702/167 |
| 5,740,503 A * | 4/1998 | Nakamura | ................ | 399/167 |
| 5,763,786 A | 6/1998 | Camplin et al. | ................ | 73/643 |
| 5,800,247 A | 9/1998 | Harms | ................ | 451/5 |
| 5,992,236 A * | 11/1999 | White et al. | ................ | 73/622 |
| 6,062,948 A | 5/2000 | Schiff et al. | ................ | 451/9 |
| 6,092,032 A | 7/2000 | Hirayama | ................ | 702/115 |
| 6,202,489 B1 * | 3/2001 | Beffy et al. | ................ | 73/628 |
| 6,206,814 B1 | 3/2001 | Tanaka et al. | | |
| 6,440,347 B1 * | 8/2002 | Izawa et al. | ................ | 264/262 |
| 6,538,774 B1 * | 3/2003 | Weidlich | ................ | 358/3.29 |
| 2003/0025781 A1 * | 2/2003 | Honma et al. | ................ | 347/213 |
| 2005/0044133 A1 * | 2/2005 | Hashimoto et al. | ........ | 709/201 |

OTHER PUBLICATIONS

Union Electric Steel Corporation, Forged Hardened Steel Rolls Service Problems Causes and Prevention, Copyright © 1999 Union Electric Steel Corporation.

* cited by examiner

*Primary Examiner*—Robert Raevis
(74) *Attorney, Agent, or Firm*—Norris, McLaughlin & Marcus

(57) ABSTRACT

A non-contact apparatus and method for precision measurement of the surface characteristics of work rolls which are used in the manufacture of sheet steel and other sheet metal products. The apparatus and method can be used to accurately measure the parameters of crown, taper, Ra, PPI, traverse, chatter, body diameter, minor defects and inclusions of a steel work roll.

19 Claims, 5 Drawing Sheets

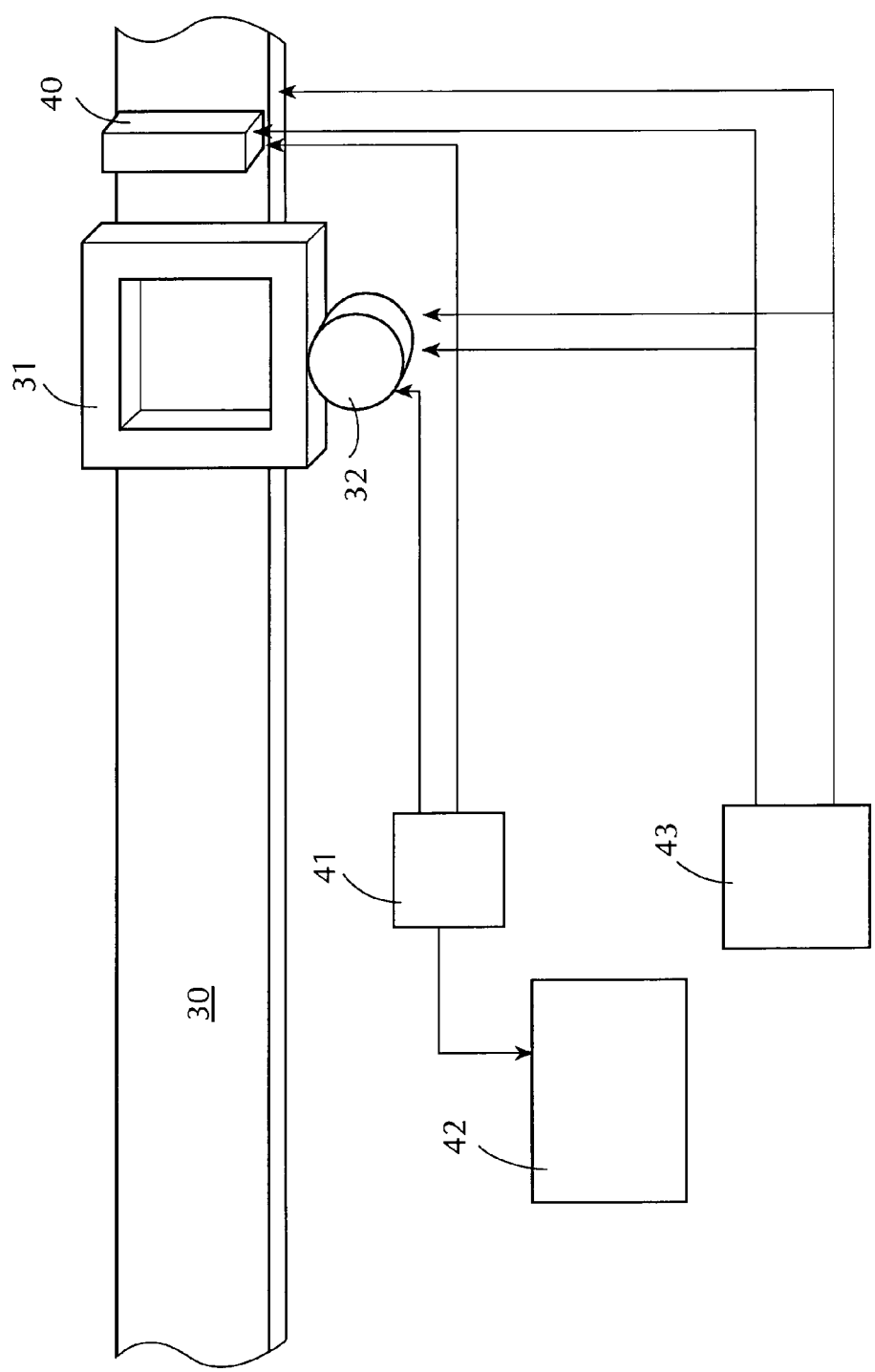

ROLL CONTOUR MEASURING APPARATUS AND METHOD

BACKGROUND OF THE INVENTION

1. Field of the Invention

This invention has to do with precision measurement of the surface characteristics of work rolls which are used in the manufacture of sheet steel and other sheet metal products. More specifically, the invention relates to a non-contact method and apparatus for measuring the crown, taper, Ra (roughness average—measured in micro-inches in the English system and micrometers in the metric system), PPI (peaks per inch in the English system or peaks per centimeter in the metric system), traverse, chafter, body diameter, minor defects and inclusions of a work roll.

2. The Related Art

In the manufacture of sheet steel, sheet aluminum and other sheet metal products, paper, plastics and other sheet materials, steel work rolls are employed in the finishing process. The roll shape and surface are machined to a high degree of accuracy. The shape of the roll, e.g., contour and taper, requires measurements on the order of $1/10,000$ inch which need to be accurate within ±3%. The surface texture, e.g., Ra and PPI, requires measurements on the order of $1/1,000,000$ inch which need to be accurate within ±3%.

Current technology employs a profilometer or other mechanical contact measuring devices to take measurements of surface properties such as Ra and PPI but such devices do not provide acceptable accuracy, repeatability or resolution for measurement of the roll surface or topography. A moving caliper, for example, is mounted on small wheels and manually moved across the surface of the work roll. A needle or a mechanical probe is maintained in contact with the surface to take measurements. Several problems are associated with use of needles, mechanical probes and other devices which are maintained in contact with the roll because manual movement causes variations in readings. In the case of the moving caliper, the wheels come under stress when going toward or away from the crown on the roll, and the crown and taper of the roll cause the measurement to be taken along a path that is not a straight line.

A non-contact gauging apparatus and method for measuring the shape of rolls and controlling machine grinding operations is described in U.S. Pat. No. 5,800,247. The apparatus requires contacting the roll at least for initial positioning and it is mounted on the grinding machine and, therefore, subjected to machining vibration.

U.S. Pat. No. 4,423,636 describes a nondestructive eddy current or articulated probe mechanism which is automatically positioned over the test roll at the grinding wheel. The system is used to detect rolling mill roll surface defects for use with a defect test system.

SUMMARY OF THE INVENTION

The present invention provides a non-contact measuring device that avoids the problems associated with the profilometer and other previously employed devices and provides more accurate, repeatable measurements of surface characteristics. The measuring device of the invention comprises a sensor mounted on a rail alongside the roll surface and it is moved along the rail, generally in parallel with the center line of the roll, traversing the surface in a straight line without coming into contact with the surface. The sensor is provided with a single or multiple probes to take measurements and sensor output is delivered to suitable software for data translation. One of the advantages of the present invention is that the designs and principles set forth herein can be applied to more accurate measuring technologies and improved software as the same develop over time.

BRIEF DESCRIPTION OF THE DRAWINGS

FIG. 3 is a diagram illustrating the relationship between the sensor of the invention, the rail, the data acquisition model, encoder and computer.

DESCRIPTION OF THE PREFERRED EMBODIMENTS

Figure 1A:
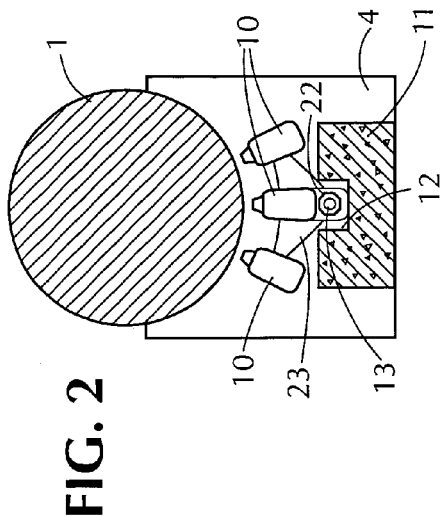
FIG. 1A is a section view taken along line A—A of FIG. 1.

The apparatus of the present invention is employed to measure work roll shape and surface characteristics such as contour, profile, crown, taper, body diameter, Ra, PPI, traverse, chatter, minor defects and inclusions. All types of commonly employed surface finishes can be measured, including finishes prepared by shot blast, EDT (electrical discharge texturing), EBT (electron beam texturing), laser texture, grinding, acid etch, peened, knurled, burnished, polished and others. Any surface topical coatings can be measured, including chrome, ceramic, nitrite and others. The roll body can be flat, concave, CVC (concave vector convex), elliptical or others. The work roll diameter typically ranges from 1 inch to 36 inches with a length from about 10 inches to about 100 inches. However, the textured surfaces of many other types and sizes of steel rolls can be measured with the apparatus of this invention such as back-up rolls which can range in diameter from 48 to 96 inches or can be larger or smaller depending upon manufacturing requirements. Accordingly, there is no limitation as to roll size in respect of the utility of the present invention and the invention can be used to measure roll characteristics regardless of the diameter of length of the roll.

The apparatus of the invention provides high resolution repeatable measurements on the order of $1/10,000$ inch for roll shape and $1/1,000,000$ inch for surface texture to an accuracy of ±1% or better. The invention comprises a permanent or portable fixture placed parallel between 2-roll journal steady rests and it can be completely independent of all work roll processing equipment or it can be incorporated as a part of such equipment. Importantly, the apparatus has non-contact measuring probes.

A suitable probe base line specification measuring range equals 0.00 "to 0.0005" with a tolerance of ±1% or better. The preferred probe base line specification measuring range equals 0.00 " to 0.00005" with a tolerance of ±0.5%. One of the preferred sensors that can be used in accordance with the invention is a capacitance sensor which is a true analog sensing device having an analog range equal to 0–10 VDC (volts direct current) with a tolerance of ±0.5% in a range of 200–300 Hz (cycles/second) or greater and less than 5 db (decibels) noise compatibility. Other sensors such as inductance or laser sensors can be employed but inductance sensors generally have less resolution because they are less stable to temperature and noise than capacitance sensors. Laser sensors can be unreliable because oil on the roll affects reflectivity. Single or multiple channel sensors can be employed. With multiple channel sensors, multiple surface characteristics can be measured simultaneously. A linear output-input single and/or multiple channel sensor amplifier is employed and suitable sensor probe interface software includes Windows 98, Windows Me, Windows 2000 and Windows XPcompatibility. Of course, other software operating systems can be employed as will be apparent to those skilled in the art.

In a preferred embodiment, a linear output device is employed having a 0–10 VDC analog output, a positioning encoder and a 16 bit analog/digital (A/D) converter is employed. In a more preferred embodiment a 64 bit A/D converter can be employed and in a most preferred embodiment a 256 bit A/D converter can be employed. As technology develops, converters with even more capacity can be employed, but for practical purposes the 16 bit embodiment is sufficient to meet or exceed current industrial requirements. An encoder interface module is used having 8 analog inputs, 8 digital outputs and a USB (universal serial buss) port connection. The data acquisition module has a minimum 16 bit resolution and takes up to about 1,000 traces/second (about 1,000 data points/second). (A 64 bit embodiment would take 4,000 data points/second, a 256 bit embodiment would take 16,000 data points/second, etc.) A linear encoder is used to establish a reference point for all subsequent measurements. All devices connected to the computer have a software interface compatible with Window 98, Windows Me, Windows 2000 and Windows XP or other operating systems which may be installed in the computer.

A suitable computer is employed which has the capacity to store at least about 1,000 traces/second (or more if desired as explained above) for each of crown, taper, Ra, PPI, traverse, body diameter and chatter. The computer has the ability to display or print individual or all traces in a layered view. We have successfully employed a computer with a Pentium IV processor 2GS (giga Hz speed), 1 gigabyte ram (random access memory), 2 USB ports, 1 parallel port, 1 LAN (local area network) port, 60 gigabyte hard disk, cdrw (compact disc read/write), 24 megabyte video high resolution driver, floppy drive, rs 232 port, 15" touch screen interface control panel, a high speed 2 ppm color high definition printer and the following:

Database storage for crown and taper profile of 1000 traces.
   Database storage for Ra and PPI profile of 1000 traces.
   Database storage for roll diameter profile of 1000 traces.
   Database storage for traverse profile of 1000 traces
   Output to display and printer of individual and or all traces in layer view.
   Output database raw data and traces in layer and or individual view to cdrw.

Of course other suitable computer systems can be employed having similar or greater capacity.

Figure 1:
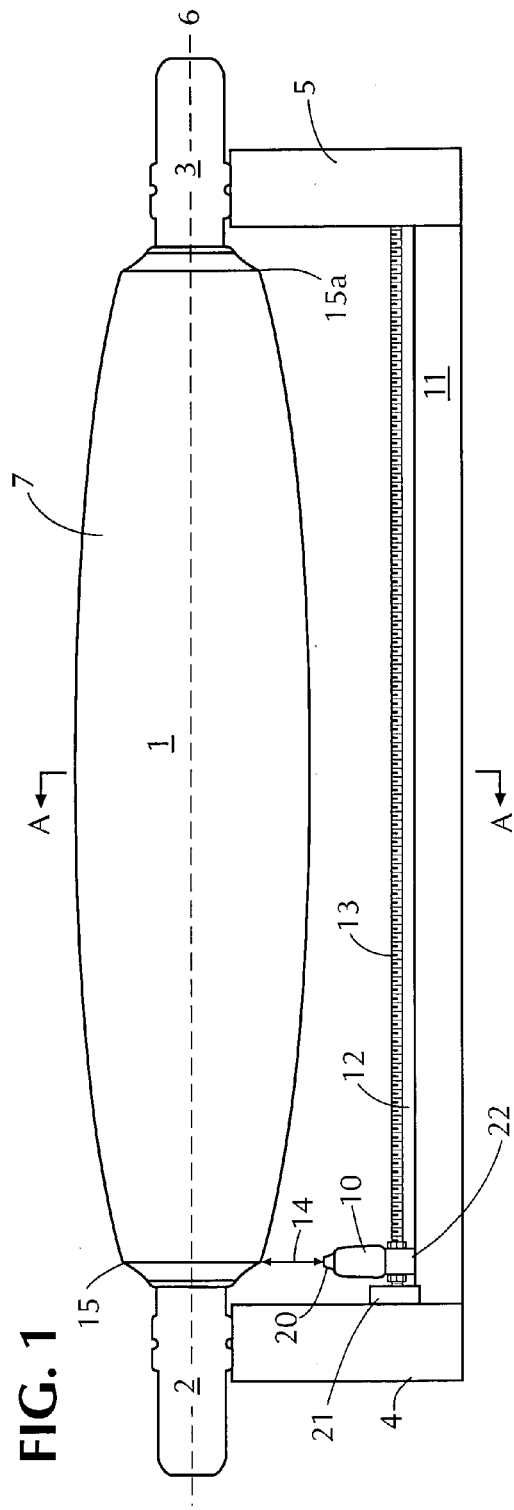
FIG. 1 is an elevational diagram of a work roll mounted on two roll journal steady rests and the sensor of the invention is on a linear gauge rail below the roll. The work roll is not drawn to scale and the crown is exaggerated for illustrative purposes.

Referring to the drawings, FIG. 1 illustrates a work roll 1 having journals 2 and 3 positioned on journal rests 4 and 5. The work surface of the roll is illustrated by the area 7. The sensor 10 is positioned on rail 11 having a groove 12. The preferred rail is constructed from granite. Linear drive mechanism 13 incorporates a positioning encoder (not shown) which is a position sensing device that provides information on where the sensor is positioned relative to the starting point (e.g., the starting point would be the zero point). The linear drive mechanism 13 is driven by a suitable driver 21 which can be a motor, servo or other device known in the art and it causes the sensor 10 to move along the groove 12 in parallel with the axis 6 of roll 1. Suitable linear drive mechanisms include a ball screw 13 (a threaded rod as shown) or a magnetic floating drive (not shown) or a pneumatic floating drive (not shown). Probe 20 on sensor 10 is positioned at a sufficient distance 14 from end reference point 15 on roll 1 so that the probe does not come into contact with the roll at any time during movement of the sensor 10 along the length of the roll. A distance 14 of about 0.1 inch is usually sufficient. Point 15a is the reference point at the other end of the roll.

Figure 2:
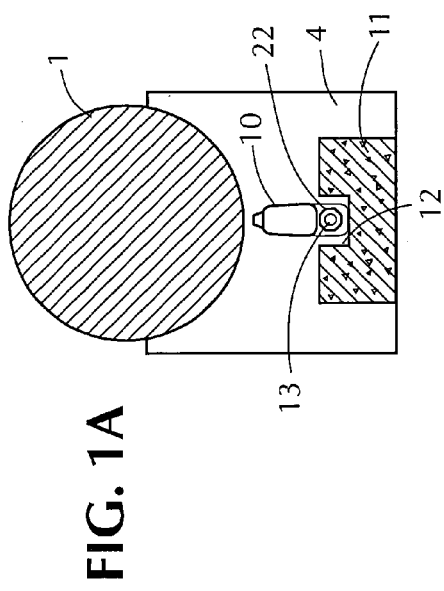
FIG. 2 is a section view similar to FIG. 1A but illustrating an embodiment with multiple sensors.

FIG. 2 illustrates an embodiment of the invention wherein three sensors 10 mounted on bracket 23 are employed. The sensors can be the same or different. For example, three capacitance sensors can be used to simultaneously measure three different surface texture parameters.

FIG. 3 is a block diagram of an embodiment of the invention wherein a linear slide 30 is provided with a slide carriage frame 31 having a capacitance sensor/probe 32 or multiple sensors/probes (not shown) mounted thereon. The slide carriage frame 31 traverses the length of the linear slide 30 which is positioned in parallel with the axis of a work roll not illustrated in FIG. 3. The capacitance sensor/probe 32 is maintained in close proximity to the surface of the work roll (not shown) in an arrangement such as that shown in FIG. 1. The linear slide can be mounted above the roll, below the roll or in any other position in parallel with the center line of the roll. The block diagram illustrates the relationship of an encoder 40, a data acquisition module 41 and a computer 42 to the capacitance sensor/probe 32. A power supply 43 is also illustrated.

Figure 4:
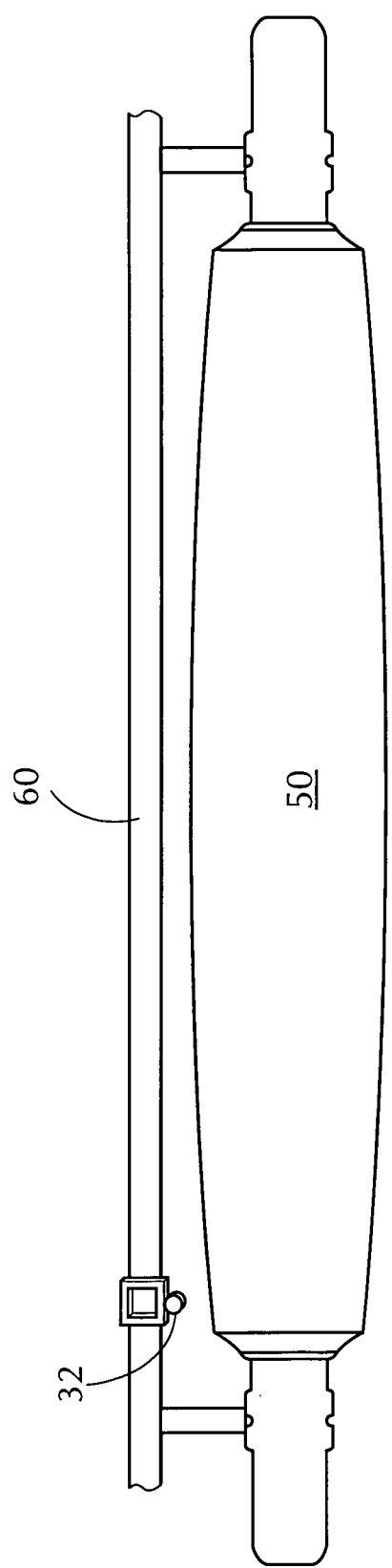
FIG. 4 is a diagram illustrating an embodiment wherein the linear gauge rail is mounted above the roll.

FIG. 4 illustrates the relationship of a work roll 50 to a linear gauge rail 60 and sensor/probe 32 in the embodiment wherein the gauge rail is positioned above the roll. As noted above, the gauge rail can be positioned at any location relative to the roll as long as it permits the sensor/probe to be moved in parallel with the axis of the roll at a suitable distance from the roll surface to permit accurate measurement of the surface characteristics.

Figure 5:
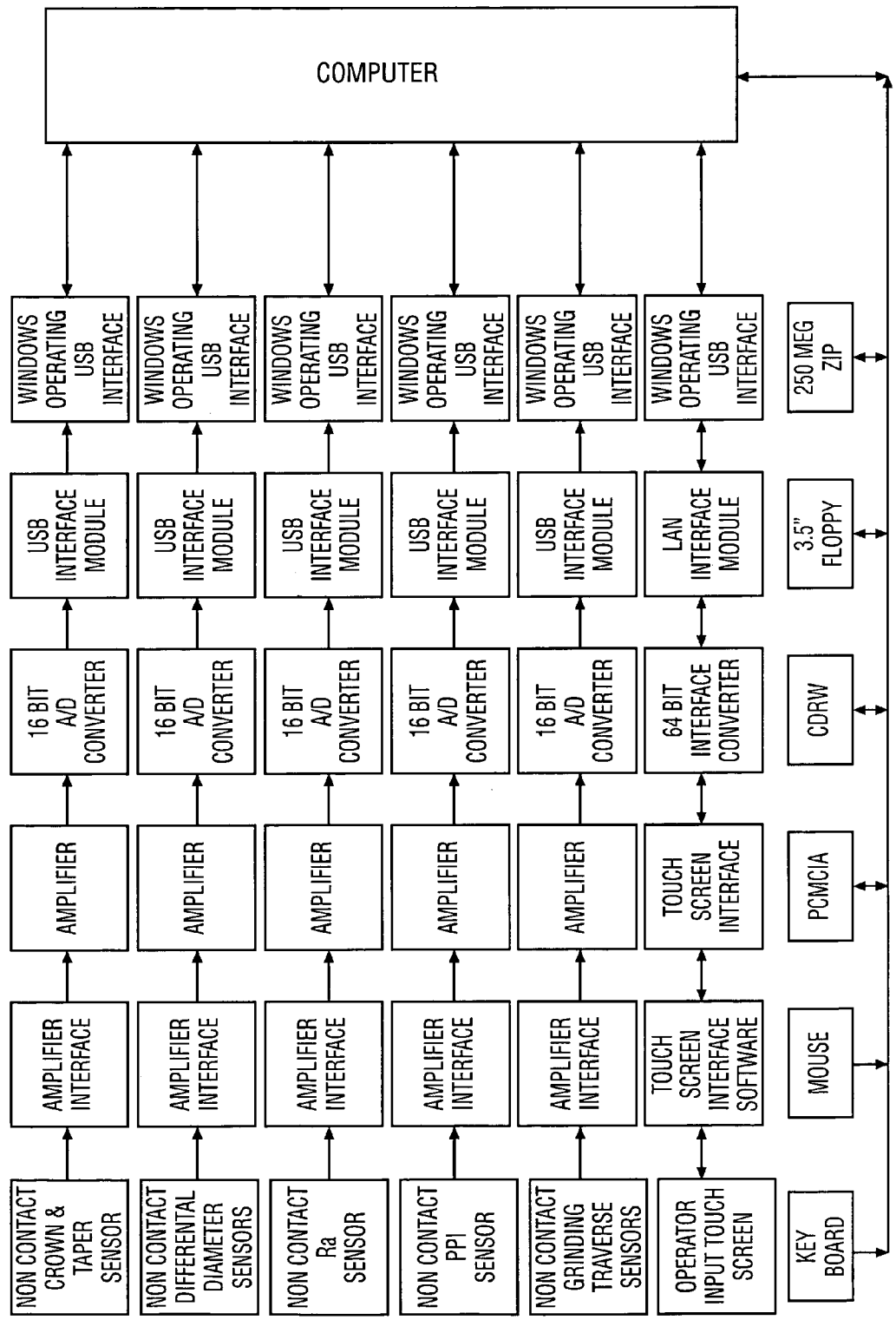
FIG. 5 is a block diagram illustrating the input interface.

FIG. 5 is a block diagram illustrating the input interfaces of various types of sensors as well as an input touch screen and features of the computer.

Figure 6:
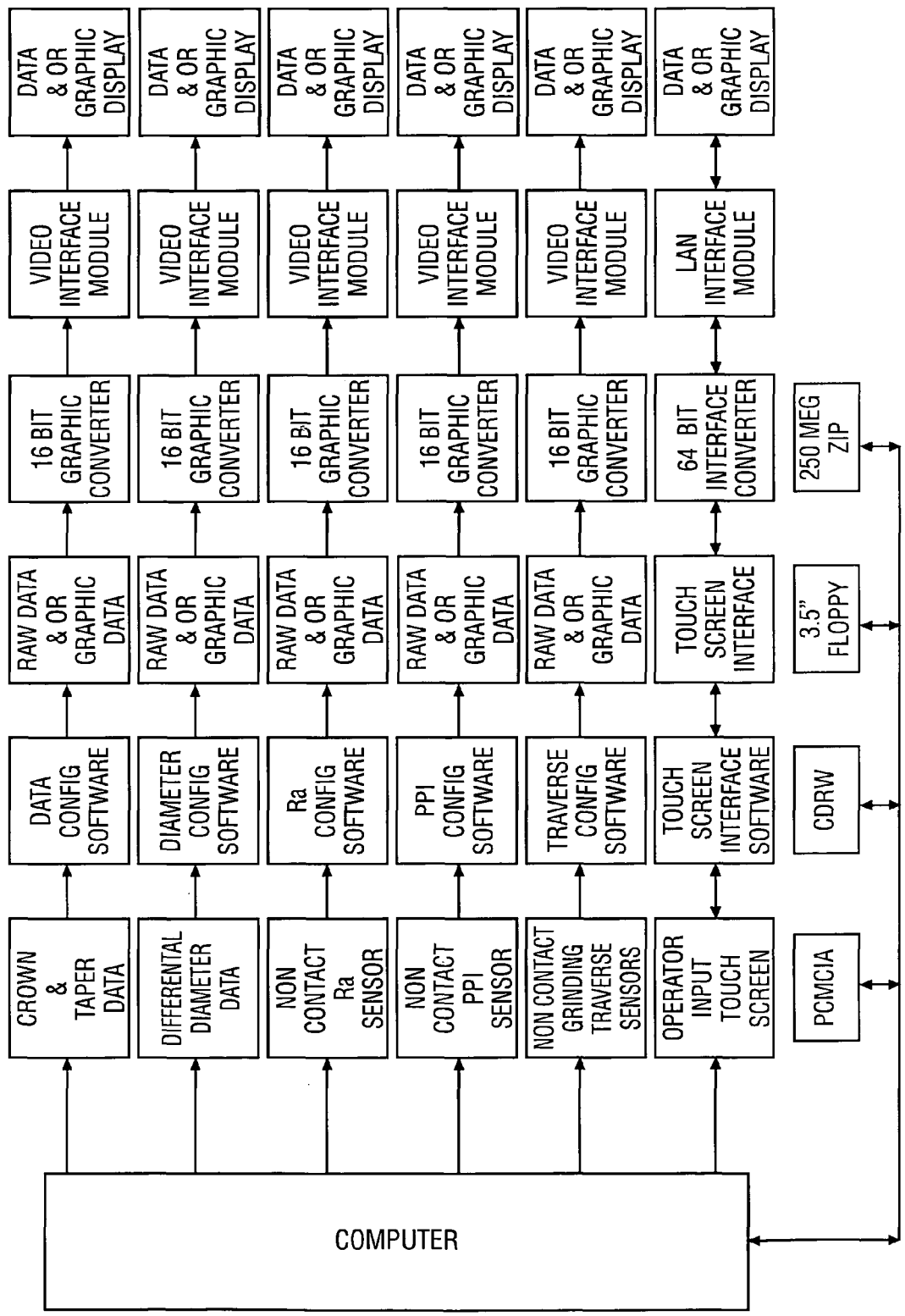
FIG. 6 is a block diagram illustrating the output interface.

FIG. 6 illustrates the output interface corresponding to the inputs illustrated in FIG. 5.

The components illustrated in FIG. 5 and FIG. 6 are off the shelf items which can be appropriately selected by those skilled in the art.

It should be noted that the apparatus of the present invention can be a stand alone apparatus which is isolated from production equipment in case vibration is caused by the production equipment that can affect the repeatability and accuracy of the measurements. The work roll is maintained in a stationary position during most measurements except for the measurement of chatter which may require rotation of the roll.

The invention claimed is:

1. A non-contact apparatus for measuring the shape or surface characteristics of a work roll used in the manufacture of sheet steel and other sheet metal products comprising
   a sensor having a non-contact measuring probe,
   a linear rail, a means for moving the sensor along the rail at a non-contact measuring distance from the surface of the work roll and in a line which is in parallel with the center line of the work roll, a means of collecting shape or surface characteristics data from the sensor and measuring a shape or surface characteristic selected from the group consisting of crown, taper, Ra, PPI, traverse, body diameter, defects and inclusions, wherein the sensor is a capacitance sensor or an inductance sensor.

2. The apparatus of claim 1 further comprising a means for positioning the rail in parallel with the center line of the roll.

3. The apparatus of claim 1 wherein the sensor is a capacitance sensor.

4. The apparatus of claim 1 further comprising a means of translating and displaying the data.

5. The apparatus of claim 1 wherein the probe base line specification measuring range equals 0.00" to 0.0005" with a tolerance of ±1%.

6. The apparatus of claim 1 wherein the probe base line specification measuring range equals 0.00" to 0.00005" with a tolerance of ±0.5%.

7. The apparatus of claim 1 further comprising a means for rotating the roll about its center line.

8. The apparatus of claim 1 wherein the sensor is an analog sensor.

9. A method of measuring the shape or surface characteristics of a work roll used in the manufacture of sheet steel and other sheet metal products comprising providing a sensor having a non-contact measuring probe with a linear rail and a means for moving the sensor along the rail at a non-contact measuring distance from the surface of the roll and in a line which is in parallel with the center line of the work roll, moving the sensor along the rail while collecting shape or surface characteristics data from the sensor, translating the data to a measurement of crown, taper, Ra, PPI, traverse, body diameter, defects and inclusions, wherein the sensor is a capacitance sensor or an inductance sensor.

10. The method of claim 9 wherein the data is displayed as a measurement of crown, taper, Ra, PPI, traverse, body diameter, defects or inclusions.

11. The method of claim 9 wherein the data is collected at a rate of about 1,000 data points per second.

12. The method of claim 9 wherein the data is collected at a rate of about 4,000 data points per second or 16,000 data points per second or more than 16,000 data points per second.

13. The method of claim 9 wherein the roll is rotated about its center line during measuring.

14. The method of claim 9 wherein the sensor is an analog sensor.

15. A non-contact apparatus for measuring the shape or surface characteristics of a work roll comprising a sensor having a non-contact measuring probe, a linear rail, a means for moving the sensor along the rail at a non-contact measuring distance from the surface of the work roll and in a line which is in parallel with the center line of the work roll, and a means of collecting shape or surface characteristics data from the sensor wherein the sensor comprises multiple measuring probes for simultaneously measuring two or more of crown, taper, Ra, PPI, traverse and body diameter.

16. A method of measuring the shape or surface characteristics of a work roll comprising providing a sensor having multiple measuring probes for simultaneously measuring two or more of crown, taper, Ra, PPI, traverse and body diameter with a linear rail and a means for moving the sensor along the rail at a non-contact measuring distance from the surface of the roll and in a line which is in parallel with the center line of the work roll, moving the sensor along the rail while collecting shape or surface characteristics data from the sensor.

17. The method of claim 16 further comprising the steps of translating and displaying the data.

18. The method of claim 16 wherein the data is collected at a rate of about 1,000 data points per second.

19. The method of claim 16 wherein the data is collected at a rate of about 4,000 data points per second or 16,000 data points per second or more than 16,000 data points per second.

* * * * *